(12) United States Patent
Simpson et al.

(10) Patent No.: US 8,673,603 B2
(45) Date of Patent: Mar. 18, 2014

(54) FERMENTATION PROCESS FOR CONTROLLING BUTANEDIOL PRODUCTION

(75) Inventors: Sean Dennis Simpson, Auckland (NZ); Christophe Collet, Auckland (NZ); Christophe Daniel Mihalcea, Auckland (NZ); Joshua Jeremy Conolly, Auckland (NZ); Guy William Waters, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 13/435,453

(22) Filed: Mar. 30, 2012

(65) Prior Publication Data

US 2012/0252082 A1 Oct. 4, 2012

Related U.S. Application Data

(60) Provisional application No. 61/470,172, filed on Mar. 31, 2011.

(51) Int. Cl.
*C12P 7/04* (2006.01)
*C12P 7/06* (2006.01)
*C12P 7/40* (2006.01)

(52) U.S. Cl.
USPC ............................. 435/157; 435/161; 435/136

(58) Field of Classification Search
None
See application file for complete search history.

(56) References Cited

U.S. PATENT DOCUMENTS

| 4,851,344 A | 7/1989 | Simon et al. |
| 2009/0029434 A1* | 1/2009 | Tsai et al. ..................... 435/170 |
| 2012/0045807 A1* | 2/2012 | Simpson et al. .............. 435/148 |

FOREIGN PATENT DOCUMENTS

| CN | WO2006133637 | 12/2006 |
| NZ | WO2007117157 | 10/2007 |
| WO | WO 0208438 A2 * | 1/2002 |
| WO | WO2008/098254 | 8/2008 |
| WO | WO2008/115080 | 9/2008 |
| WO | WO2009/151342 | 12/2009 |
| WO | WO2010/071697 | 6/2010 |
| WO | WO2012/015317 | 2/2012 |

OTHER PUBLICATIONS

Syu MJ, Appl Microbiol Biotechnol 55:10-18 (2001), Qin et al., Chinese J Chem Eng 14(1):132-136 (2006).
Abrini et al *Clostridium autoethanogenum*, sp. Nov., An Anaerobic Bacterium That Produces Ethanol From Carbon Monoxide; Arch. Microbiol., 161: 345-351 (1994).

* cited by examiner

*Primary Examiner* — David J Steadman
*Assistant Examiner* — Paul Holland
(74) *Attorney, Agent, or Firm* — Frank S. Mohuaro

(57) ABSTRACT

Methods for improving the efficiency of 2,3-butanediol fermentations are disclosed. More specifically methods of increasing the butanediol productivity from the anaerobic fermentation of a substrate comprising carbon monoxide or carbon monoxide and hydrogen by one or more caboxydotrophic acetogenic bacteria are disclosed. The method includes supplying a hydrogen depleted substrate to increase butanediol productivity. The method includes producing butanediol at a volumetric productivity rate of at least 15 g/L/day.

6 Claims, 4 Drawing Sheets

FERMENTATION PROCESS FOR CONTROLLING BUTANEDIOL PRODUCTION

CROSS REFERENCE TO RELATED APPLICATION

This application claims priority to U.S. Application Ser. No. 61/470,172, filed on Mar. 31, 2011 which is incorporated by reference in its entirety.

FIELD OF THE INVENTION

This invention relates to the production of 2,3-butanediol by microbial fermentation of substrates comprising carbon monoxide or carbon monoxide and hydrogen.

BACKGROUND OF THE INVENTION

Biofuels for transportation are attractive replacements for gasoline and are rapidly penetrating fuel markets as low concentration blends. Biofuels, derived from natural plant sources, are more environmentally sustainable than those derived from fossil resources (such as gasoline), their use allowing a reduction in the levels of so-called fossil carbon dioxide ($CO_2$) gas that is released into the atmosphere as a result of fuel combustion. In addition, biofuels can be produced locally in many geographies, and can act to reduce dependence on imported fossil energy resources. Alcohols suitable for use as biofuels include ethanol, butanol and 2,3-butanediol.

Ethanol is rapidly becoming a major hydrogen-rich liquid transport fuel around the world. Worldwide consumption of ethanol in 2002 was an estimated 10.8 billion gallons. The global market for the fuel ethanol industry is also predicted to grow sharply in future, due to an increased interest in ethanol in Europe, Japan, the USA and several developing nations.

Butanediols including 1,2-butanediol, 1,3-butanediol, 1,4-butanediol and 2,3-butanediol may be considered to have a variety of advantages over ethanol. Like ethanol, butanediols may be used directly as an automotive fuel additive. They may also be relatively easily transformed into a number of other potentially higher value and/or higher energy products. For example, 2,3-butanediol may be readily converted in a two step process into an eight-carbon dimer which can be used as aviation fuel.

2,3-butanediol derives its versatility from its di-functional backbone, i.e., 2 hydroxyl groups are located at vicinal C-atoms allowing the molecule to be transformed quite easily into substances such as butadiene, butadione, acetoin, methyl-ethyl ketone etc. These chemical compounds are used as base molecules to manufacture a vast range of industrially produced chemicals.

In addition, 2,3-butanediol may be used as a fuel in an internal combustion engine. It is in several ways more similar to gasoline than it is to ethanol. As the interest in the production and application of environmentally sustainable fuels has strengthened, interest in biological processes to produce 2,3-butanediol (often referred to as bio-butanol) has increased.

2,3-butanediol can be produced by microbial fermentation of carbohydrate containing feedstock (Syu M J, *Appl Microbiol Biotechnol* 55:10-18 (2001), Qin et al., *Chinese J Chem Eng* 14(1):132-136 (2006)). 2,3-butanediol may also be produced by microbial fermentation of biomass from crops such as sugar beet, corn, wheat and sugarcane. However, the cost of these carbohydrate feed stocks is influenced by their value as human food or animal feed and the cultivation of starch or sucrose-producing crops for 2,3-butanediol production is not economically sustainable in all geographies. Therefore, it is of interest to develop technologies to convert lower cost and/or more abundant carbon resources into 2,3-butanediol.

Carbon Monoxide (CO) is a major by-product of the incomplete combustion of organic materials such as coal or oil and oil derived products. Although the complete combustion of carbon containing precursors yields CO2 and water as the only end products, some industrial processes need elevated temperatures favouring the build up of carbon monoxide over $CO_2$. One example is the steel industry, where high temperatures are needed to generate desired steel qualities. For example, the steel industry in Australia is reported to produce and release into the atmosphere over 500,000 tonnes of CO annually.

Furthermore, CO is also a major component of syngas, where varying amounts of CO and $H_2$ are generated by gasification of a carbon-containing fuel. For example, syngas may be produced by cracking the organic biomass of waste woods and timber to generate precursors for the production of fuels and more complex chemicals.

The release of CO into the atmosphere may have significant environmental impact. In addition, emissions taxes may be required to be paid, increasing costs to industrial plants. Since CO is a reactive energy rich molecule, it can be used as a precursor compound for the production of a variety of chemicals. However, this valuable feedstock has not been utilised to produce 2,3-butanediol.

It is an object of the present invention to provide a process that goes at least some way towards overcoming the above disadvantages or at least to provide the public with a useful choice.

SUMMARY OF THE INVENTION

In a first broad aspect of the invention, there is provided a method for increasing the efficiency of butanediol production by microbial fermentation of a substrate comprising CO and $H_2$. In particular embodiments, the invention provides a method of controlling the production of butanediol by microbial fermentation, the method including:
  i) providing a substrate comprising CO and $H_2$; and
  ii) in a bioreactor containing a culture of one or more micro-organisms, anaerobically fermenting the substrate to produce butanediol; and one or more co-products;
wherein the butanediol productivity in step (ii) is affected by the composition of the substrate of step (i).

In one embodiment the one or more co-products is alcohol(s) and/or acid(s).

In one embodiment the one or more co-products is ethanol.

In one embodiment the one or more co-products is acetic acid.

In one embodiment the $H_2$ composition of the substrate of (i) affects the butanediol productivity.

In one embodiment of the invention, providing a substrate which has a high $H_2$ concentration decreases the 2,3-butanediol productivity.

In one embodiment of the invention there is provided a method for increasing butanediol productivity by microbial fermentation, the method including:
  (i) providing a $H_2$ depleted substrate comprising CO;
  (ii) in a bioreactor containing a culture of one or more carboxydotrophic acetogenic bacteria, anaerobically fermenting the substrate to produce butanediol.

In one embodiment the substrate comprises less than 20% $H_2$ by volume, less than 15% $H_2$ by volume, less than 10% $H_2$ by volume, less than 5% $H_2$ by volume, or less than 2% $H_2$ by volume.

In one embodiment the specific uptake of $H_2$ is less than 1000 mmol/L/day, less than 500 mmol/L/day, less than 300 mmol/L/day, less than 200 mmol/L/day or less than 100 mmol/L/day.

In one embodiment the 2,3-butanediol productivity is at least 20 g/L/day, at least 25 g/L/day, at least 30 g/L/day, at least 35 g/L/day, at least 40 g/L/day, or at least 45 g/L/day.

In one embodiment the concentration of 2,3-butanediol in the fermentation broth is at least 2 g/L, at least 4 g/L, at least 6 g/L, at least 8 g/L or at least 10 g/L.

In another embodiment of the invention there is provided a method for decreasing the butanediol productivity by microbial fermentation, the method including:
(i) providing a substrate rich in $H_2$;
(ii) in a bioreactor containing a culture of one or more micro-organisms, anaerobically fermenting the substrate.

In one embodiment, the substrate comprises at least 20% $H_2$ by volume, at least 25% $H_2$ by volume, at least 30% $H_2$ by volume, at least 35% $H_2$ by volume, at least 40% $H_2$ by volume, at least 45% $H_2$ by volume or about 50% $H_2$ by volume.

In one embodiment the specific uptake of $H_2$ is at least 2500 mmol/L/day, at least 3000 mmol/L/day, at least 3500 mmol/L/day, at least 4000 mmol/L/day, at least 4500 mmol/L/day or at least 5000 mmol/L/day.

In one embodiment the 2,3-butanediol productivity is less than 15 g/L/day, less than 10 g/L/day, less than 5 g/L/day, less than 3 g/L/day or less than 1 g/L/day.

In one embodiment the concentration of 2,3-butanediol in the fermentation broth is less than 2 g/L, or less than 1 g/L or around 0 g/L.

In a second broad aspect of the invention there is provided a method of producing one or more products by microbial fermentation, the method comprising at lest the steps of:
(a) providing a substrate containing carbon monoxide or carbon monoxide and hydrogen; and
(b) in a bioreactor containing a culture of one or more carboxydotrophic acetogenic bacteria anaerobically fermenting the substrate to produce 2,3-butanediol and one or more co-products;
wherein the 2,3-butanediol productivity increases in correlation with the age of the cells provided in the fermenter.

In one embodiment the one or more co-products is alcohol(s) and/or acid(s).

In one embodiment the one or more co-products is ethanol.

In one embodiment the one or more co-products is acetic acid.

In one embodiment of the invention, the average age of the cells in the bioreactor is increased by the use of a cell recycle member. A skilled person would understand that cell recycle members may include, but are not limited to cell recycle membranes or disc-stack centrifugal separators.

In one embodiment the 2,3-butanediol productivity is increased when the average age of the cells in the bioreactor increases In one embodiment of the invention the 2,3-butanediol productivity is inhibited when the average age of the cells in the bioreactor is lower.

Although the invention is broadly as defined above, it is not limited thereto and also includes embodiments of which the following description provides examples.

BRIEF DESCRIPTION OF THE DRAWINGS

The invention will now be described in more detail and with reference to the accompanying figures, in which.

DETAILED DESCRIPTION OF THE INVENTION

Figure 1:
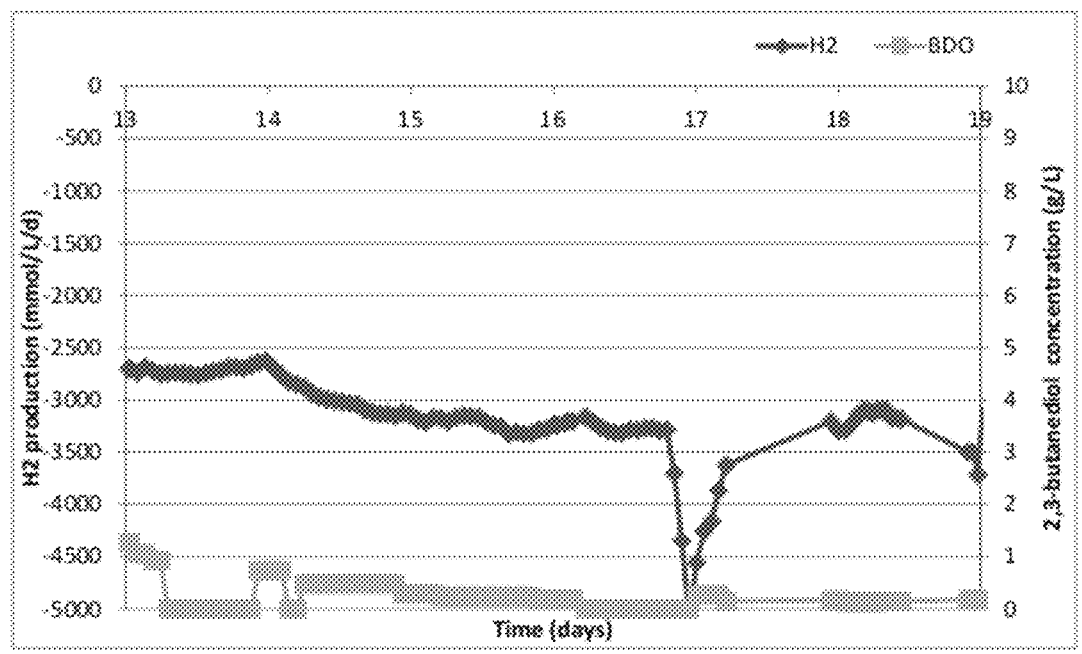
FIG. 1 is a graphical representation showing a decreased 2,3-butanediol concentration in a bioreactor with a high hydrogen uptake.

The following is a description of the present invention, including preferred embodiments thereof, given in general terms. The invention is further exemplified in the disclosure given under the heading "Examples" herein below, which provides experimental data supporting the invention, specific examples of aspects of the invention, and means of performing the invention.

As used herein "butanediol" refers to all structural isomers of the diol including 1,2-butanediol, 1,3-butanediol, 1,4-butanediol and 2,3-butanediol and stereoisomers thereof. The term "2,3-butanediol" should be interpreted to include all enantiomeric and diastereomeric forms of the compound, including (R,R), (S,S) and meso forms, in racemic, partially stereoisomerically pure or substantially stereoisomerically pure forms.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

The term "substrate" and like terms should be understood to include any substrate in which carbon monoxide and/or hydrogen is available to one or more strains of bacteria for growth and/or fermentation, for example.

"Gaseous substrates comprising carbon monoxide" or "gaseous substrate comprising at least CO" include any gas which contains a level of carbon monoxide. The gaseous substrate will typically contain a major proportion of CO, preferably at least about 10% to about 95% CO by volume.

"Gaseous substrates comprising hydrogen" include any gas which contains a level of hydrogen.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated butanediol concentrations, the volume of desired product produced per volume of substrate consumed, the rate of production or level of production of the desired product, and the relative proportion of the desired product produced compared with other by-products of the fermentation.

"butanediol productivity" or "rate of butanediol production" is the volumetric productivity of butanediol. In continuous systems the volumetric productivity is calculated as the ratio of the steady state butanediol concentration and the liquid retention time. In batch systems the volumetric productivity is calculated as the butanediol concentration and the time required to produce said concentration in a batch system. The volumetric productivity is reported as g/L/day.

Unless the context requires otherwise, the phrases "fermenting", "fermentation process" or "fermentation reaction" and the like, as used herein, are intended to encompass both the growth phase and product biosynthesis phase of the process.

The Hydrogen Depleted Substrate

The inventors have surprisingly shown the production of 2,3-butanediol by microbial fermentation of *Clostridium autoentanogenum*. In particular, the inventors have determined that the production of 2,3-butanediol can be controlled by certain factors. According to one aspect of the invention they have demonstrated that the amount of 2,3-butanediol produced can be increased or decreased by controlling the hydrogen composition of the gaseous substrate. According to a second aspect of the invention they have demonstrated that the age of the microbial cells in the bioreactor and the growth phase of the microbial culture has an effect on the amount of 2,3-butanediol produced by the cells.

It has been shown that the 2,3-butanediol productivity can be increased by providing a H2 depleted substrate. The inventors have demonstrated that the 2,3-butanediol productivity increases when the amount of hydrogen in the substrate is limited. The inventor determined that 2,3-butanediol production is increased when the hydrogen composition of the gaseous substrate is less than 20% $H_2$ by volume, less than 15% $H_2$ by volume, less than 10% $H_2$ by volume, less than 5% $H_2$ by volume, or less than 2% $H_2$ by volume.

A correlation between the 2,3-butanediol productivity and the hydrogen uptake of the bacterial culture has also been determined. In particular it has been shown that the 2,3-butanediol productivity is increased when the uptake of $H_2$ is less than 1000 mmol/L/day, less than 500 mmol/L/day, less than 300 mmol/L/day, less than 200 mmol/L/day or less than 100 mmol/L/day.

The inventors have demonstrated 2,3-butanediol productivity of at least 15 g/L/day, at 20 g/L/day, at least 25 g/L/day, at least 30 g/L/day, at least 35 g/L/day, at least 40 g/L/day, or at least 45 g/L/day when hydrogen uptake is limited. In one embodiment the concentration of 2,3-butanediol in the fermentation broth is at least 2 g/L, at least 4 g/L, at least 6 g/L, at least 8 g/L or at least 10 g/L.

The Hydrogen Rich Substrate

Correspondingly it has been shown that increasing the $H_2$ composition of the gaseous substrate has a negative impact on 2,3-butanediol productivity. In one embodiment the 2,3-butanediol productivity is less than 10 g/L/day, less than 5 g/L/day, less than 3 g/L/day or less than 1 g/L/day. In one embodiment the concentration of 2,3-butanediol in the fermentation broth is less than 2 g/L, or less than 1 g/L or around 0 g/L.

Fermentations utilising substrates having an increased hydrogen composition showed decreased 2,3-butanediol productivity. Substrates having a hydrogen composition of greater than 25% $H_2$ by volume, or greater than 30% $H_2$ by volume, or greater than 40 $H_2$ by volume, or greater than 45% $H_2$ by volume or greater than 50% $H_2$ by volume had an inhibitory effect on the volumetric productivity of the culture.

An increase in the specific uptake of $H_2$ similarly impacted on the 2,3-butanediol productivity. In cultures where the uptake of hydrogen is at least 2500 mmol/L/day, at least 3000 mmol/L/day, at least 3500 mmol/L/day, at least 4000 mmol/L/day, at least 4500 mmol/L/day or at least 5000 mmol/L/day, the 2,3-butanediol productivity is lower than in cultures having a lower hydrogen uptake.

In a second aspect of the present invention, it has been demonstrated that 2,3-butanediol productivity is increased when the growth of the bacterial culture has substantially ceased. The inventors have surprisingly shown that the age of the cells in culture has an effect on volumetric productivity of the cells. The volumetric 2,3-butanediol productivity of the cells less than 80 hours is markedly lower than the volumetric productivity of older cells. The 2,3-Butandiol productivity is improved in cell cultures having an average cell age of greater than 90 hours, or greater than 100 hours, or greater than 110 hours. In one embodiment the 2,3-butanediol productivity is greater than 6 g/L/day, greater than 8 g/L/day, greater than 10 g/L/day, greater than 12 g/L/day, greater than 14 g/L/day or greater than 16 g/L/day.

In one embodiment of the invention the 2,3-butanediol productivity is lower when the average age of the cells in the bioreactor is lower. In one embodiment of the invention the 2,3-butanediol productivity is lower when the average age of the cells in the bioreactor is less than 80 hours, or less than 60 hours, or less than 40 hours, less than 30 hours, less than 20 hours or less than 10 hours. In one embodiment of the 2,3-butanediol productivity is less than 4 g/L/day, less than 3 g/L/day, less than 2 g/L/day or less than 1 g/L/day.

Furthermore the 2,3-butanediol:ethanol ratio is improved in cultures having an older population of cells. In fermentation it has been shown that the ratio improves in favour of 2,3-butanediol production as the culture ages. Cell cultures having an average cell age of less than 90 hours show an 2,3-butanediol to ethanol ratio of around 1:10, or around 1:15, or around 1:20, or around 1:25. Cell cultures having an average cell age of greater than 100 hours shows a marked improvement in favour of 2,3-butanediol with a ratio of 1:6, or around 1:5, or around 1:4, around 1:3, around 1:2 or around 1:1.

In one embodiment of the invention, the average age of the cells in the bioreactor is increased by the use of a cell retention means. Cell retention means are well known in the art, but exemplary cell retention means include cross-flow membranes and/or hollow fibre membranes.

Micro-Organisms

In one embodiment, the one or more microorganisms is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium coskatii, Butyribacterium limosum, Butyribacterium methylotrophicum, Acetobacterium woodii, Alkalibaculum bacchii, Blautia producta, Eubacterium limo-* sum, *Moorella thermoacetica, Moorella the rmautotrophica, Oxobacter pfennigii,* and *Thermoanaerobacter kiuvi*

In embodiments of the invention the one or more microorganisms used in the fermentation is *Clostridium autoethanogenum*. In a preferred embodiment the *Clostridium autoethanogenum* is a *Clostridium autoethanogenum* having the identifying characteristics of the strain deposited at the German Resource Centre for Biological Material (DSMZ) under the identifying deposit number 19630. In another embodiment the *Clostridium autoethanogenum* is a *Clostridium autoethanogenum* having the identifying characteristics of DSMZ deposit number DSMZ 23693.

The address of the German Resource Centre for Biological Material (DSMZ) is DSMZ GmbH InhoffenstratBe, 7 B, D-38124 Braunschweig, Germany The microorganism was deposited on 07 Jun. 2010.

Culturing of the bacteria used in a method of the invention may be conducted using any number of processes known in the art for culturing and fermenting substrates using anaerobic bacteria. Exemplary techniques are provided in the "Examples" section of this document. By way of further example, those processes generally described in the following articles using gaseous substrates for fermentation may be utilised: K. T. Klasson, M. D. Ackerson, E. C. Clausen and J. L. Gaddy (1991). Bioreactors for synthesis gas fermentations resources. Conservation and Recycling, 5; 145-165; K. T. Klasson, M. D. Ackerson, E. C. Clausen and J. L. Gaddy (1991). Bioreactor design for synthesis gas fermentations. Fuel. 70. 605-614; K. T. Klasson, M. D. Ackerson, E. C. Clausen and J. L. Gaddy (1992). Bioconversion of synthesis gas into liquid or gaseous fuels. Enzyme and Microbial Technology. 14; 602-608; J. L. Vega, G. M. Antorrena, E. C. Clausen and J. L. Gaddy (1989). Study of Gaseous Substrate Fermentation: Carbon Monoxide Conversion to Acetate. 2. Continuous Culture. Biotech. Bioeng. 34. 6. 785-793; J. L. Vega, E. C. Clausen and J. L. Gaddy (1989). Study of gaseous substrate fermentations: Carbon monoxide conversion to acetate. 1. Batch culture. Biotechnology and Bioengineering. 34. 6. 774-784; and, J. L. Vega, E. C. Clausen and J. L. Gaddy (1990). Design of Bioreactors for Coal Synthesis Gas Fermentations. Resources, Conservation and Recyling. 3. 149-160. Methods for culturing bacteria on substrates comprising carbohydrates are also well known in the art.

Substrates

In one embodiment of the invention, 2,3-butanediol is produced by microbial fermentation of a substrate comprising carbohydrate using *Clostridium autoethanogenum*. It will be appreciated there are many examples of carbohydrates suitable for fermentation known in the art and many examples of the types of processes used to ferment the carbohydrate substrate. By way of example, suitable substrates may include, but are not limited to, monosaccharides such as glucose and fructose, oligosaccharides such as sucrose or lactose, polysaccharides, such as cellulose or starch. Although it is contemplated that all of these carbohydrate substrates (and mixtures thereof) are suitable in the present invention, preferred carbohydrate substrates are glucose, fructose and sucrose (and mixtures thereof).

Those skilled in the art will appreciate fermentable sugars may be obtained from cellulosic and lignocellulosic biomass through processes of pre-treatment and saccharification, as described, for example, in US20070031918. Biomass refers to any cellulose or lignocellulosic material and includes materials comprising cellulose, and optionally further comprising hemicellulose, lignin, starch, oligosaccharides and/or monosaccharides. Biomass includes, but is not limited to bioenergy crops, agricultural residues, municipal solid waste, industrial solid waste, sludge from paper manufacture, yard waste, wood and forestry waste.

However, in a preferred embodiment of the invention commercially available fructose is used as the carbon and energy source for the fermentation.

In a preferred embodiment, a substrate comprising carbon monoxide or carbon monoxide and hydrogen, preferably a gaseous substrate comprising carbon monoxide or carbon monoxide and hydrogen is used in the methods of the invention. The gaseous substrate is preferably a waste gas obtained as a by-product of an industrial process, or from some other source such as from combustion engine (for example automobile) exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the substrate may be captured from the industrial process before it is emitted into the atmosphere, using any convenient method. Depending on the composition of the gaseous substrate, it may also be desirable to treat it to remove any undesired impurities, such as dust particles before introducing it to the fermentation. For example, the gaseous substrate may be filtered or scrubbed using known methods.

In other embodiments of the invention, the gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In particular embodiments, CO is supplied at a level sufficient for 2,3-butanediol production to occur. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained. Those skilled in the art will appreciate methods of supplying CO, particularly gaseous CO, such that the required uptake rate is achieved. However, by way of example, factors such as increasing gas hold-up in a fermentation media will increase the amount of CO available for conversion to products by the microbial culture. Furthermore, supplying CO at a faster rate or a higher partial pressure will also increase the CO availability in a fermentation broth.

To improve the efficiency of the 2,3-butanediol fermentation the substrate will typically contain a minimal proportion of $H_2$, such as less than 20% $H_2$ by volume, less than 15% $H_2$ by volume, less than 10% $H_2$ by volume, less than 5% $H_2$ by volume, or less than 2% $H_2$ by volume, or substantially no $H_2$.

It has been demonstrated that excess $H_2$ has an inhibitory effect on the 2,3-butanediol productivity. $H_2$ uptake of greater than 0.10 mmol/g/min; or greater than 0.11 mmol/g/min; or greater than 0.12 mmol/g/min; or greater than 0.15 mmol/g/min has been shown to inhibit the 2,3-butanediol productivity.

In particular embodiments, $H_2$ is supplied at a depleted level to enhance the 2,3-butanediol productivity. In particular embodiments, $H_2$ is provided such that a specific uptake rate of less 0.09 mmol/g/min; or less than 0.08 mmol/g/min; or less than 0.07 mmol/g/min; or less than 0.05 mmol/g/min; or less than 0.01 mmol/g/min.

The gaseous substrate may also contain some $CO_2$ for example, such as about 1% to about 80% by volume, or 1% to about 30% by volume. In one embodiment it contains about 5% to about 10% by volume. In another embodiment the gaseous substrate contains approximately 20% $CO_2$ by volume.

Typically, the carbon monoxide will be added to the fermentation reaction in a gaseous state. However, the invention should not be considered to be limited to addition of the substrate in this state. For example, the carbon monoxide could be provided in a liquid. For example, a liquid may be saturated with a carbon monoxide containing gas and then that liquid added to a bioreactor. This may be achieved using standard methodology. By way of example a microbubble dispersion generator (Hensirisak et. al. Scale-up of microbubble dispersion generator for aerobic fermentation; *Applied Biochemistry and Biotechnology* Volume 101, Number 3 October, 2002) could be used.

In one embodiment of the invention, the inventors have determined that 2,3-butanediol can be produced by fermentation of a first substrate and a second substrate. In one particular embodiment of the invention, 2,3-butanediol will be produced when a first substrate, preferably a carbohydrate and more preferably fructose and a second substrate, preferably a substrate comprising CO, are provided.

In a further embodiment, the inventors have determined that 2,3-butanediol will be produced by a first substrate and on complete consumption, the first substrate may be replaced with a second substrate and the 2,3-butanediol continues to be produced. In a preferred embodiment, the first substrate is fructose and on complete consumption of the fructose, a substrate comprising CO can be provided. The inventors have surprisingly found that 2,3-butanediol continues to be produced. The inventors further contemplate that the first substrate and second substrate may be alternated if needed. For example if a first substrate is unavailable, an alternative substrate may be used until the availability of the first substrate improves.

Media

It will be appreciated that for growth of the bacteria and substrate to butanediol fermentation to occur, in addition to the substrate, a suitable nutrient medium will need to be fed to the bioreactor. A nutrient medium will contain components, such as vitamins and minerals, sufficient to permit growth of the micro-organism used. Anaerobic media suitable for the growth of *Clostridium autoethanogenum* are known in the art, as described for example by Abrini et al (*Clostridium autoethanogenum*, sp. Nov., An Anaerobic Bacterium That Produces Ethanol From Carbon Monoxide; *Arch. Microbiol.*, 161: 345-351 (1994)). The "Examples" section herein after provides further examples of suitable media.

Fermentation Conditions

The fermentation should desirably be carried out under appropriate conditions for the substrate to butanediol fermentation to occur. Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The inventors have determined that, in one embodiment where pH is not controlled, there does not appear to be a deleterious effect on 2,3-butanediol production.

Bioreactor

Fermentation reactions may be carried out in any suitable bioreactor as described previously herein. In some preferred embodiments of the invention, the bioreactor may comprise a first, growth reactor in which the micro-organisms are cultured, and a second, fermentation reactor, to which broth from the growth reactor is fed and in which most of the fermentation product (2,3-butanediol, for example) is produced.

Cell Retention Means

According to one embodiment of the invention, the bioreactor is configured to enable the accumulation of cells, thus increasing the average age of the cells in the bioreactor. Cell retention means are well known in the art, but exemplary cell retention means include cross-flow membranes and/or hollow fibre membranes.

Product Recovery

The fermentation will result in a fermentation broth comprising a desirable product (such as butanediol) and/or one or more by-products (such as ethanol, acetate and butyrate) as well as bacterial cells, in a nutrient medium. In a preferred embodiment, the fermentation products include 2,3-butanediol.

2,3-butanediol, or a mixed alcohol stream containing 2,3-butanediol and one or more other alcohols, may be recovered from the fermentation broth by methods known in the art, such as fractional distillation or evaporation, pervaporation, and extractive fermentation. By-products such as acids including acetate and butyrate may also be recovered from the fermentation broth using methods known in the art. For example, an adsorption system involving an activated charcoal filter or electrodialysis may be used.

In certain preferred embodiments of the invention, 2,3-butanediol and by-products are recovered from the fermentation broth by continuously removing a portion of the broth from the bioreactor, separating microbial cells from the broth (conveniently by filtration, for example), and recovering 2,3-butanediol and optionally other alcohols and acids from the broth. Alcohols may conveniently be recovered for example by distillation, and acids may be recovered for example by adsorption on activated charcoal. The separated microbial cells are preferably returned to the fermentation bioreactor. The cell free permeate remaining after the alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted during recovery of 2,3-butanediol and/or by-products, the pH should be re-adjusted to a similar pH to that of the broth in the fermentation bioreactor, before being returned to the bioreactor.

The invention will now be described in more detail with reference to the following non-limiting examples.

EXAMPLES

Example 1

Materials and Methods

TABLE 1

Media

| Medium component | Per L of medium |
|---|---|
| Stem solution 3 | 8.33 mL |
| Stem solution 4 | 8.33 mL |
| $CH_3COONH_4$ | 3.00 g |
| Resazurin solution (1 g/L) | 1.00 mL |
| $H_3PO_4$ (85%) | 0.37 mL |
| Metal solution 1 | 1.00 mL |
| Metal solution 2 | 0.10 mL |
| Sodium tungstate solution (2.94 g/L) | 0.10 mL |
| Composite B-vitamin solution | 10.00 mL |
| Reverse osmosis water | Up to 1 L |

| | Per L of stock |
|---|---|
| Stem solution 3 | |
| $MgCl_2 \cdot 6H_2O$ | 10.18 g |
| $CaCl_2 \cdot 2H_2O$ | 14.70 g |
| Stem solution 4 | |
| NaCl | 12.00 g |
| KCl | 15.00 g |
| Metal solution 1 | |
| $FeSO_4 \cdot 7H_2O$ | 0.10 g |
| $ZnSO_4 \cdot 7H_2O$ | 0.20 g |
| $NiCl_2 \cdot 6H_2O$ | 0.02 g |
| HCl (38%) | 30 mL |
| Metal solution 2 | |
| $MnSO_4 \cdot H_2O$ | 0.50 g |
| $CoCl_2 \cdot 6H_2O$ | 0.20 g |
| $H_3BO_3$ | 0.30 g |
| $NaMoO_4 \cdot 2H_2O$ | 0.03 g |
| $Na_2SeO_3$ | 0.02 g |
| HCl (38%) | 5.00 mL |
| Composite B-vitamin solution | |
| Biotin | 20 mg |
| Folic acid | 20 mg |
| Pyridoxine | 10 mg |
| Thiamine | 50 mg |
| Riboflavin | 50 mg |
| Niacin | 50 mg |
| Pantothenic acid | 50 mg |
| Vitamin $B_{12}$ | 50 mg |
| 4-Aminobenzoic acid | 50 mg |
| Lipoic acid | 50 mg |

Bioreactor Medium Preparation:

Stem solution 3, stem solution 4, ammonium acetate, resazurin, phosphoric acid and reverse osmosis water were added to a 2 L fermentation vessel sparged with $N_2$ gas. The medium was constantly stirred, heated to 37° C. and pH adjusted to 5.3 using $NH_4OH$ (5 M). Metal solution 1, metal solution 2, sodium tungstate solution and composite B-vitamin solution were then added and sparged for >2 h with $N_2$ gas. The medium was then sparged with steel mill gas containing $H_2$ (3%), $N_2$ (30%), CO (47%) and $CO_2$ (20%) and reduced to an oxidation-reduction potential (ORP) of approximately 200 mV (Ag/AgCl electrode) using a $Cr^{2+}$ solution.

Bacteria:

*Clostridium autoethanogenum* were obtained from the German Resource Centre for Biological Material (DSMZ). The accession number given to the bacteria is DSMZ 10061.

Fermentation in Bioreactor:

The prepared medium was inoculated with bacteria from an actively dividing culture and supplied with a sulphur source by way of $Na_2S$ (0.5 M) addition. $NH_4OH$ (5 M) was used to maintain a pH of 5.0 and the broth temperature was set to 37° C. throughout the fermentation. Gas input rates and compositions, as well as medium feed rates were adjusted in response to the cultures requirements or for experimental purposes. This fermentation also utilized a cell recycle membrane to continuously draw broth permeate, whilst retaining bacterial cells.

Sampling and Analytical Procedures:

Liquid culture samples were taken at differing intervals over a 41 day period. These samples were used to establish the optical density at 600 nm (spectrophotometer) and the level of substrates and products (high performance liquid chromatography—HPLC).

HPLC was routinely used to quantify the level of acetate, ethanol and 2,3-butanediol. The input and output gas compositions were analysed using a gas chromatographer (GC), allowing measurement of CO and $H_2$ consumption and $CO_2$ production by the culture.

Figure 2:
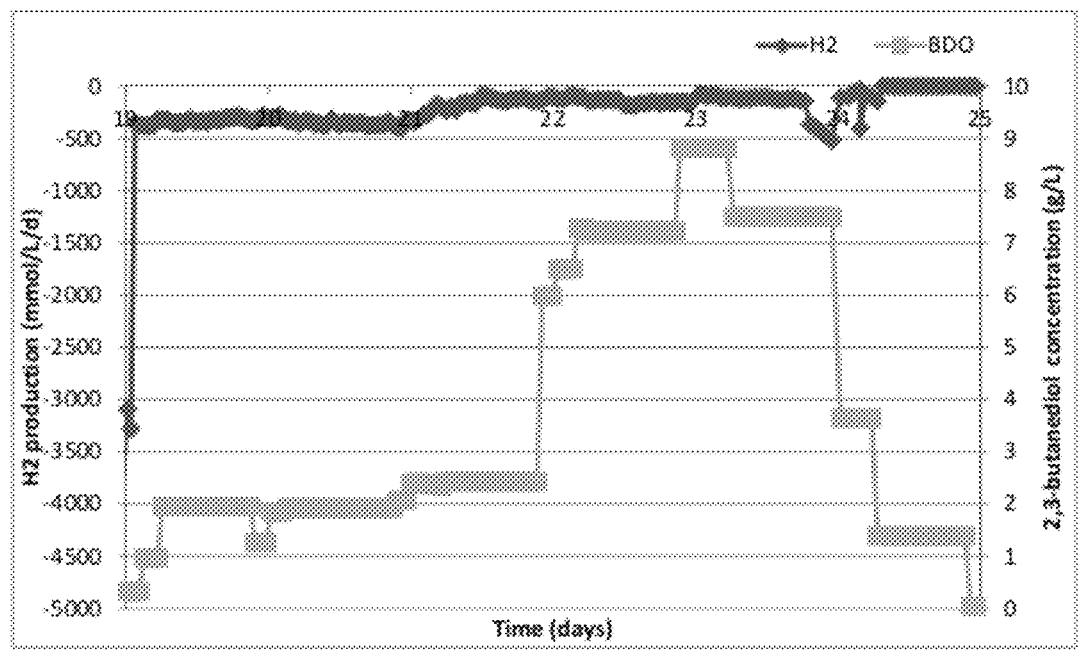
FIG. 2 is a graphical representation demonstrating an increased 2,3-butanediol concentration in a bioreactor with a low hydrogen uptake.
Figure 3:
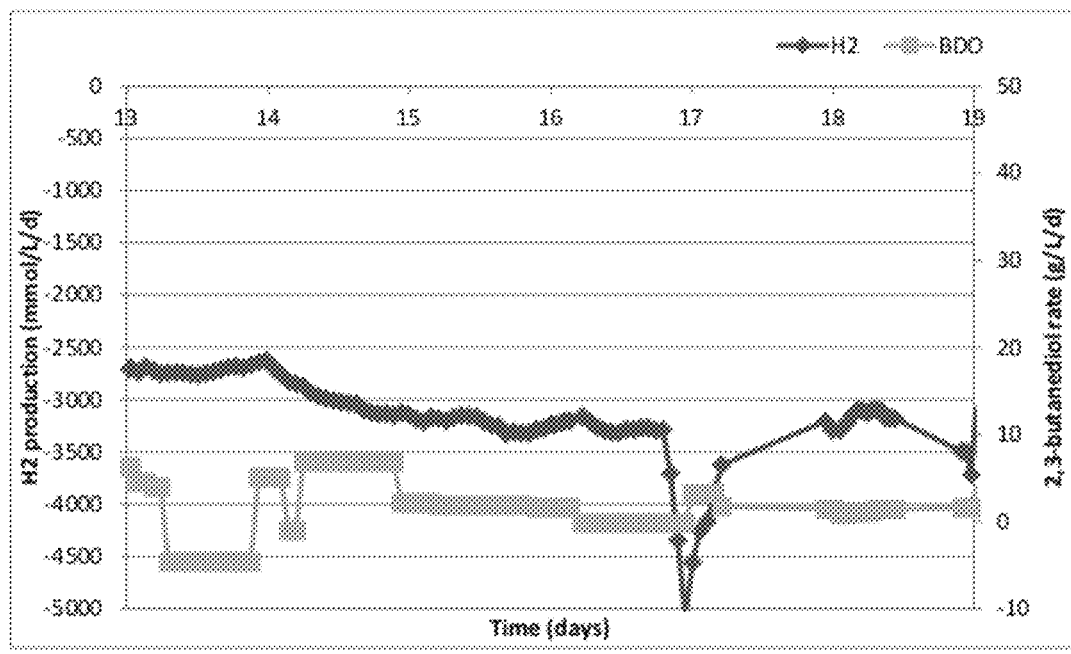
FIG. 3 a graphical representation showing a decreased rate of 2,3-butanediol production in a bioreactor with a high hydrogen uptake.
Figure 4:
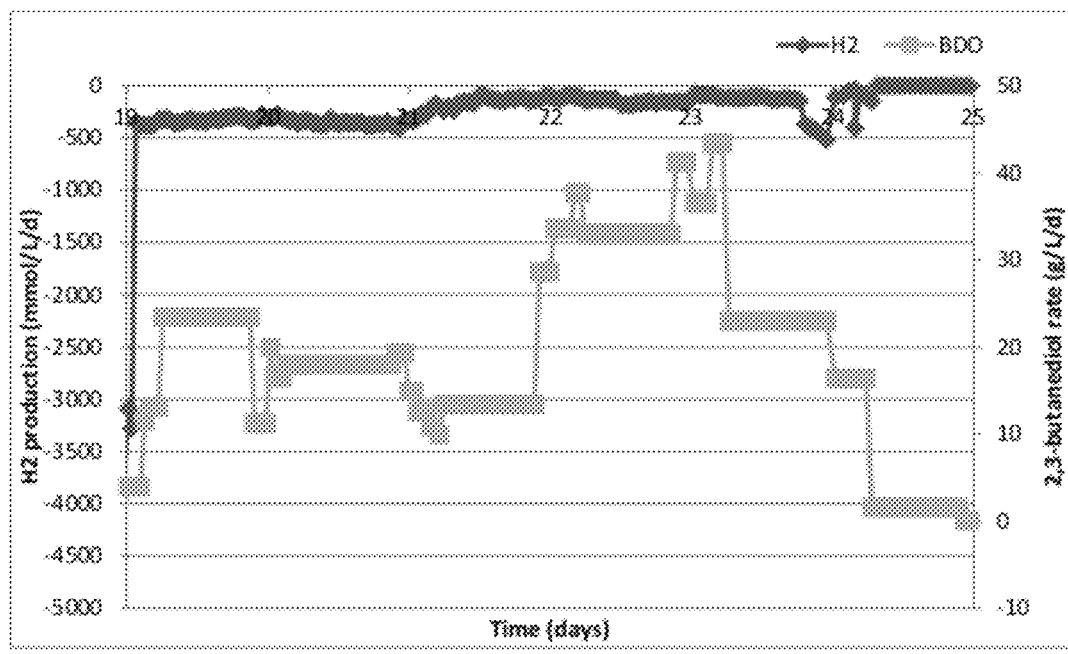
FIG. 4 is a graphical representation demonstrating an increased rate of 2,3-butanediol production in a bioreactor with a low hydrogen uptake.

FIGS. 1 to 6 demonstrate the ability to control the 2,3-butanediol productivity by altering the uptake of H2 in the bioreactor. FIGS. 1 and 3 show a fairly stable uptake of Hydrogen at a rate of around 3000 mmol/L/day, the resulting concentration of 2,3-butanediol is less than 1 g/L, and the 2-3-butandiol productivity is less than 7 g/L/day. FIGS. 2 and 4 show a bioreactor with a Hydrogen uptake of between around 400 mmol/L/day and around 0 mmol/L/day. The resulting 2,3-butanediol concentration is between 2 g/L and 9 g/L, and the 2,3-butandiol productivity increase to 10 g/L/day. FIG. 4 demonstrates an increase in 2,3-butandiol productivity to around 45 g/L/day.

Figure 5:
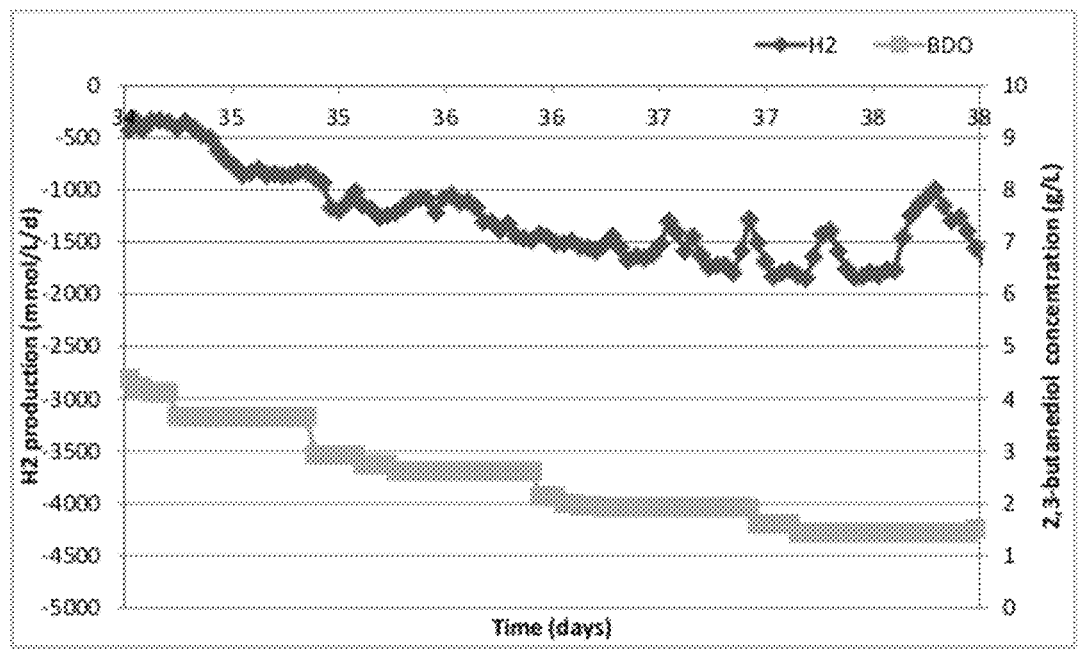
FIG. 5 is a graphical representation of demonstrating a increase in hydrogen uptake and a corresponding decrease in 2,3-butanediol concentration.
Figure 6:
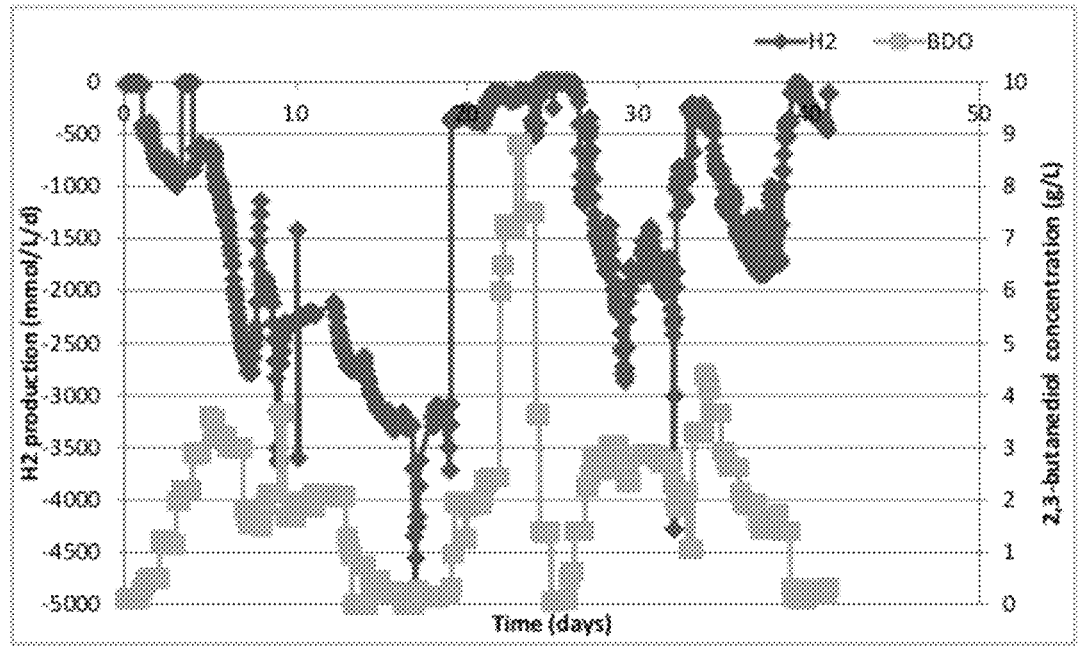
FIG. 6 is a graphical representation showing the correlation between hydrogen uptake and 2,3-butanediol concentration over 42 days.

FIG. 5 shows a bioreactor with a steadily increasing rate of hydrogen uptake, and a level of 2,3-butanediol which steadily decreases in line with the increased Hydrogen uptake. FIG. 4 shows a bioreactor experiment run over 42 days clearly showing the correlation between decreased Hydrogen uptake and increased levels of 2,3-butanediol.

Example 2

Figure 7:
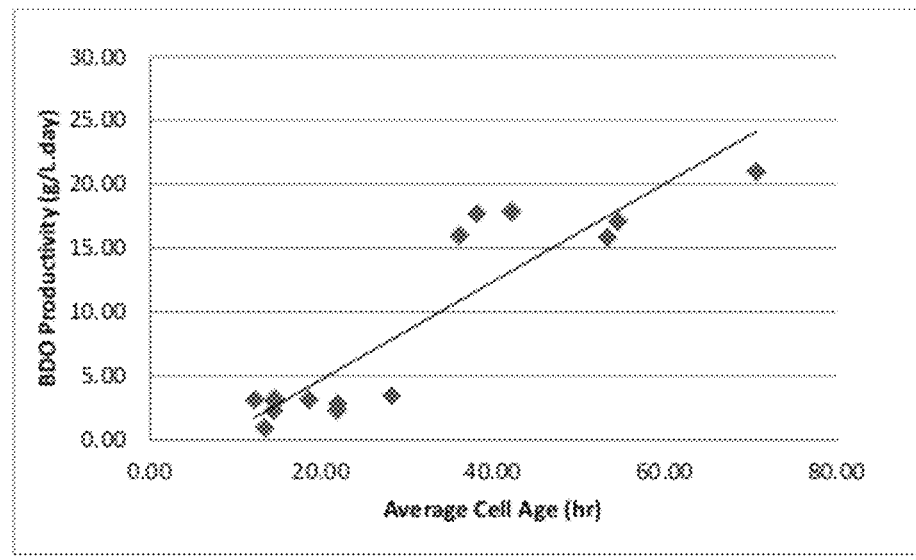
FIG. 7 is a graphical representation showing a correlation between 2,3-butanediol and cell age in the first reactor of a two reactor system.
Figure 8:
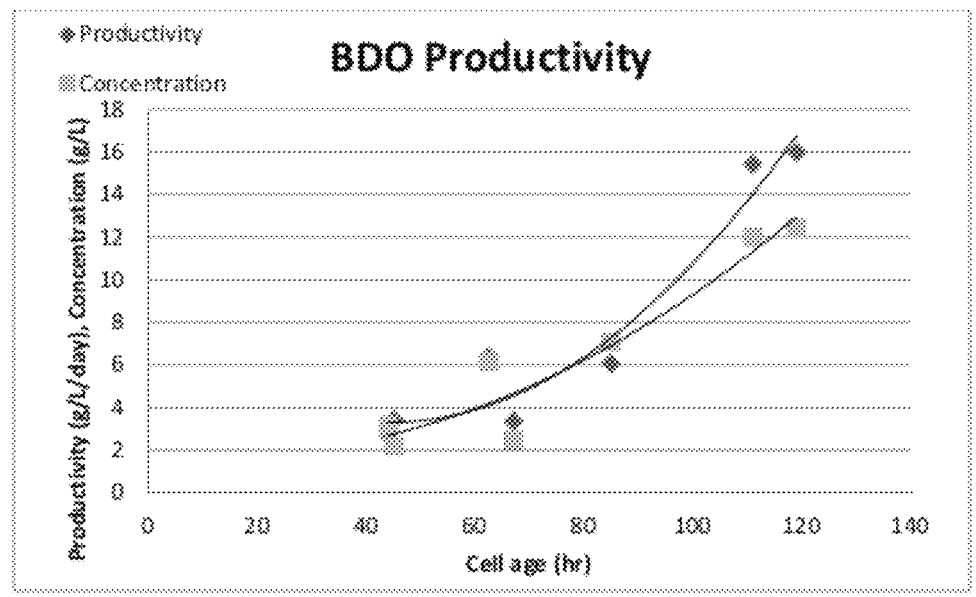
FIG. 8 is a graphical representation showing concentration and volumetric productivity of 2,3-Butandiol over various cell ages in the second reactor of a two reactor system.

FIGS. 7-8 and Table 2 demonstrate 2,3-butanediol and ethanol levels in two reactor systems in accordance with one embodiment of the present invention.

FIG. 7 correlates the relationship between 2,3-butanediol and cell age in the first fermenter of a two reactor system. FIG. 7 shows a steady increase in the production rate of 2,3-butandediol in the first reactor as the age of the cells in the fermenter increases.

FIG. 8 shows the rate of production and the concentration of 2,3-butanediol in the second fermenter of a two reactor system. FIG. 8 demonstrates increased 2,3-butanediol concentration in the fermentation broth as well as an increased rate of production of 2,3-butanediol as the cell age in the fermenter increases.

Table 2 demonstrates the correlation between cell age and 2,3-butanediol as well as the effect of high ethanol productivity in a two reactor system. Table 2 shows that high ethanol productivity in the first reactor of a two reactor system relates to high 2,3-butanediol production over the whole system, whereas 2,3-butanediol productivity is lower over the whole system when the productivity in the first reactor is low, and the average cell age is low.

TABLE 2

| Ethanol Productivity in first reactor (g/L/day) | Ethanol Productivity in second reactor (g/L/day) | Average Productivity (g/L/day) | Average Cell age (hr) | Butanediol to ethanol ratio |
|---|---|---|---|---|
| 22.50 | 70.00 | 46.25 | 41.55 | 1:10 |
| 35.71 | 119.04 | 77.38 | 45.12 | 1:23 |
| 34.01 | 103.39 | 68.70 | 62.50 | 1:11 |
| 61.04 | 101.03 | 81.03 | 67.00 | 1:24 |
| 27.37 | 85.19 | 56.28 | 84.90 | 1:9 |
| 47.33 | 81.96 | 64.64 | 86.20 | 1:20 |
| 110.43 | 54.48 | 82.46 | 110.98 | 1:5 |
| 105.96 | 58.44 | 82.46 | 110.98 | 1:5 |
| 106.99 | 10.55 | 58.77 | 169.00 | 1:5 |

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method of producing 2,3-butanediol by microbial fermentation of a substrate comprising at least CO and $H_2$, the method comprising:
   a) passing the substrate into a bioreactor comprising a culture of at least one *Clostridium* bacteria; and
   b) anaerobically fermenting the substrate to produce 2,3-butanediol and at least one co-product, wherein the substrate is provided such that a specific rate of hydrogen uptake from 0 mmol/L/day to 400 mmol/L/day by the culture is maintained and produces from 2 g/L/day to 45 g/L/day of 2,3-butanediol.

2. The method of claim 1 wherein the *Clostridium* bacteria is selected from the group consisting of *Clostridium autoethanogenum*, *Clostridium ljungdahlii*, *Clostridium ragsdalei*, *Clostridium carboxidivorans*, *Clostridium drakei*, *Clostridium Scatologenes*, and *Clostridium coskatii*.

3. The method of claim 1 wherein the *Clostridium* bacteria is *Clostridium autoethanogenum* strain deposited at the German Collection of Microorganisms and Cell Cultures (DSMZ) under the accession number DSM 23693.

4. The method of claim 1 further comprising adding a cell retention membrane to the bioreactor, wherein the cell retention membrane is selected from the group consisting of cross-flow membranes and hollow fiber membranes, thereby increasing the average age of the bacterial cells.

5. The method of claim 1, wherein the co-product is selected from the group consisting of alcohols, acids, and mixtures thereof.

6. The method of claim 5, wherein the alcohol is ethanol.

* * * * *